United States Patent
Rodrigo Cavalin et al.

(10) Patent No.: US 11,216,768 B2
(45) Date of Patent: Jan. 4, 2022

(54) PRODUCT QUALITY ANALYSIS AND CONTROL

(71) Applicant: International Business Machines Corporation, Armonk, NY (US)

(72) Inventors: Paulo Rodrigo Cavalin, Rio de Janiero (BR); Carmen Nilda Mena Paz, Rio de Janiero (BR); Jaione Tirapu Azpiroz, Rio de Janiero (BR); Ana Paula Appel, São Paulo (BR); Alexandre Alves, São Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 20 days.

(21) Appl. No.: 16/887,607

(22) Filed: May 29, 2020

(65) Prior Publication Data

US 2021/0374646 A1 Dec. 2, 2021

(51) Int. Cl.
| | |
|---|---|
| G06Q 10/06 | (2012.01) |
| G06Q 50/28 | (2012.01) |
| G01N 33/14 | (2006.01) |
| G01N 33/52 | (2006.01) |
| G06Q 10/08 | (2012.01) |

(52) U.S. Cl.
CPC ..... *G06Q 10/06395* (2013.01); *G01N 33/146* (2013.01); *G01N 33/523* (2013.01); *G06Q 10/0833* (2013.01); *G06Q 50/28* (2013.01)

(58) Field of Classification Search
CPC ........... G06Q 10/00–50/00; G06N 1/00–35/00
See application file for complete search history.

(56) References Cited

U.S. PATENT DOCUMENTS

| | | |
|---|---|---|
| 7,424,399 B2 | 9/2008 | Kahn et al. |
| 7,881,960 B2 | 2/2011 | Ramamurti |

(Continued)

FOREIGN PATENT DOCUMENTS

CN 103797499 A 5/2014

OTHER PUBLICATIONS

C. Zhang. D. P. Bailey, and K. S. Suslick. Colorimetric sensor arrays for the analysis of beers: A feasibility study, J. Agric. Food Chem., vol. 54, No. 14, pp. 4925-4931, 2006. (Year: 2006).*

(Continued)

*Primary Examiner* — Alan S Miller
(74) *Attorney, Agent, or Firm* — Cantor Colburn LLP; Joseph Petrokaitis

(57) ABSTRACT

A product quality analysis and control system is provided. The product quality analysis and control system includes a processing system that is configured to receive data of objective qualities of a product from multiple data gathering modules. Each of the multiple data gathering modules is respectively positioned at corresponding nodes of a supply chain and is configured to receive from sensors data of objective qualities of a product when the product is at each of the corresponding nodes. The processing system includes a model repository and a data evaluation module. The data evaluation module is configured to select, from the model repository, a model associated with a type of the product and to use the model to analyze the data to identify changes in the objective qualities along the supply chain.

18 Claims, 6 Drawing Sheets

(56) References Cited

U.S. PATENT DOCUMENTS

| | | | |
|---|---|---|---|
| 8,287,897 B2* | 10/2012 | Fukui | A23L 27/86 |
| | | | 424/439 |
| 8,377,314 B2 | 2/2013 | Frank | |
| 8,751,636 B2 | 6/2014 | Tseng et al. | |
| 9,528,935 B2 | 12/2016 | Pulyassary | |
| 10,217,117 B2 | 2/2019 | Heath | |
| 2006/0047454 A1* | 3/2006 | Tamaki | G06Q 10/06 |
| | | | 702/84 |
| 2010/0107785 A1* | 5/2010 | Kugimiya | G01N 27/327 |
| | | | 73/865.7 |
| 2012/0116565 A1* | 5/2012 | Bippert | G06Q 10/06 |
| | | | 700/103 |
| 2012/0198684 A1* | 8/2012 | Carrilho | B01L 3/502707 |
| | | | 29/527.1 |
| 2013/0041899 A1* | 2/2013 | Simske | H04L 67/22 |
| | | | 707/736 |
| 2014/0062666 A1* | 3/2014 | Patterson | G06K 7/10366 |
| | | | 340/10.1 |
| 2015/0094219 A1* | 4/2015 | Trowell | C12Q 1/66 |
| | | | 506/9 |
| 2016/0327538 A1* | 11/2016 | La Valle Sansone | G01N 33/12 |
| 2016/0367988 A1* | 12/2016 | Azpiroz | G01N 27/44743 |
| 2018/0114168 A1* | 4/2018 | Ryan | G06Q 10/08 |
| 2018/0197129 A1* | 7/2018 | Appel | G06Q 10/06315 |
| 2019/0082722 A1* | 3/2019 | Sakaki | G01N 33/02 |
| 2019/0145947 A1* | 5/2019 | Oltyan | G01N 35/00871 |
| | | | 73/61.46 |
| 2019/0302008 A1* | 10/2019 | Ohta | G01N 21/251 |
| 2019/0329955 A1* | 10/2019 | Thompson | B65D 51/248 |

OTHER PUBLICATIONS

G. Sehra, M. Cole, and J. W. Gardner, Miniature taste sensing system based on dual SH-SAW sensor device: An electronic tongue, Sens. Actuators B, vol. 103, No. 1-2, pp. 233-239, 2004. (Year: 2004).*

Q. Liu, D. Zhang, F. Zhang. Y. Zhao, K. J. Hsia, and P. Wang, Biosensor recording of extracellular potentials in the taste epithelium for bitter detection, Sens. Actuators B. vol. 176, pp. 497-504, 2013. (Year: 2013).*

Andres-Iglesias et al., New trends in beer flavour compound analysis. Published online in Wiley OnlineLibrary: J Sci Food Agric 2015; 95: pp. 1571-1576.

Anonymous, "Alcohol and extract meter: Alex 500," Anton-Parr. com; URL: https://www.anton-paar.com/us-en/products/details/alcohol-and-extract-meter-alex-500/; Retrieved Mar. 27, 2020, 8 pages.

Anonymous, "Taste Sensing System TS-5000Z," Higuchi Inc.; URL: https://www.higuchi-inc.co.jp/assets/img/business_products/pharma/analysis/taste_sensing_system_english_detail_ts5000z.jpeg; Retrieved: Mar. 27, 2020; 1 page.

Blanco et al., "Sensory Characterization of Commercial Lager Beers and Their Correlations with Iso-α-Acid Concentrations". Journal of Food and Nutrition Research, 2015, vol. 3, No. 1, pp. 1-8. DOI:10.12691/jfnr-3-1-1.

Carey et al., "Rapid Identification of Bacteria with a Disposable Colorimetric Sensing Array," Journal of the American Chemical Society, 2011, pp. 7571-7576.

Ceto et al., "Application of an Electronic Tongue towards the analysis of brandies," Analytical Methods, Feb. 2013, 30 pages.

Chen et al., "Low cost smart phone diagnostics for food using paper-based colorimetric sensor arrays," Food Control, vol. 82, Dec. 2017, pp. 227-232.

Giovenzana et al., "Rapid evaluation of craft beer quality during fermentation process by vis/NIR spectroscopy". Journal of Food Engineering 142 (2014) pp. 80-86.

Gonzalez Viejo et al., "Assessment of beer quality based on foamability and chemical composition using computer vision algorithms, near infrared spectroscopy and machine learning algorithms". J Sci Food Agric (2017). 10 pages.

Latha et al., "Electronic tongue: An analytical gustatory tool," Journal of Advanced Pharmaceutical Technology & Research, 2012, 14 pages.

Nery et al., "Integrated, paper-based potentiometric electronic tongue for the analysis of beer and wine," Analytica Chimica Acta, vol. 918, Apr. 28, 2016, pp. 60-68.

Olaniran et al., "Flavour-active volatile compounds in beer:production, regulation and control". J. Inst. Brew. 2017; 123: p. 13-23.

Podrazka et al., "Electronic Tongue—A Tool for All Tastes?" MDPI, Biosensors, Dec. 31, 2017, pp. 1-24.

Toko et al., "Taste Sensor: Electronic Tongue with Global Selectivity," IEEE Sensors Journal, vol. 13, No. 8, Aug. 2016.

Wannenmacher et al., "Phenolic Substances in Beer: Structural Diversity, Reactive Potential and Relevance for Brewing Process and Beer Quality". Comprehensive Reviews in Food Science and Food Safety. vol. 17, 2018. pp. 953-988. doi: 10.1111/1541-4337.12352.

* cited by examiner

PRODUCT QUALITY ANALYSIS AND CONTROL

BACKGROUND

The present invention generally relates to programmable computers, and more specifically to a computer-based quality analysis and control system that analyzes social network data and sensorial trait data to perform product quality analysis and control.

Various kinds of products are produced in bulk then shipped to businesses and/or consumers using various modes of transportation along a supply chain. The time the product spends in the supply chain depends on multiple factors including, but not limited to, distances between the producers and the product's destination, the availability of transportation, and efficiencies at each node between the producers and the product's destination. Some qualities of the product can be measured objectively, and the ability to do so depend on a variety of factors, including, for example, initial qualities of the product at the time it's produced, the stability of the product over time, the time the product spend in the supply chain, and the conditions in which the product is stored.

SUMMARY

Embodiments of the present invention are directed to a product quality analysis and control system. A non-limiting example of the product quality analysis and control system includes a processing system that is configured to receive data of objective qualities of a product from multiple data gathering modules. Each of the multiple data gathering modules is respectively positioned at corresponding nodes of a supply chain and is configured to receive from sensors data of objective qualities of a product when the product is at each of the corresponding nodes. The processing system includes a model repository and a data evaluation module. The data evaluation module is configured to select, from the model repository, a model associated with a type of the product and to use the model to analyze the data to identify changes in the objective qualities along the supply chain.

Embodiments of the present invention are directed to a sensor for use in a beverage quality analysis and control system. A non-limiting example of the sensor includes a stem, one or more foldable strips and one or more visual sensors. The one or more foldable strips respectively extend from the stem and respectively include a sensor element to sense an objective quality of the beverage and an indicator element to be indicative of a reading of the sensor element. Each of the one or more foldable strips is configured to be anchored on a beverage container rim with the sensor and indicator elements in and outside the beverage, respectively. The one or more visual sensors are disposed on or partially framed by the stem.

Embodiments of the invention are directed to a beverage quality analysis and control method for use with a supply chain of producers, distributors and consumers at nodes of the supply chain. A non-limiting example of the beverage quality analysis and control method includes sensing objective qualities of a beverage at each node, gathering data of the objective qualities at each node and forwarding the data from each node to a network for reception by a processing system, selecting, at the processing system, a model associated with a type of the beverage from a model repository and using the model to analyze the data to identify changes in the objective qualities along the supply chain.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
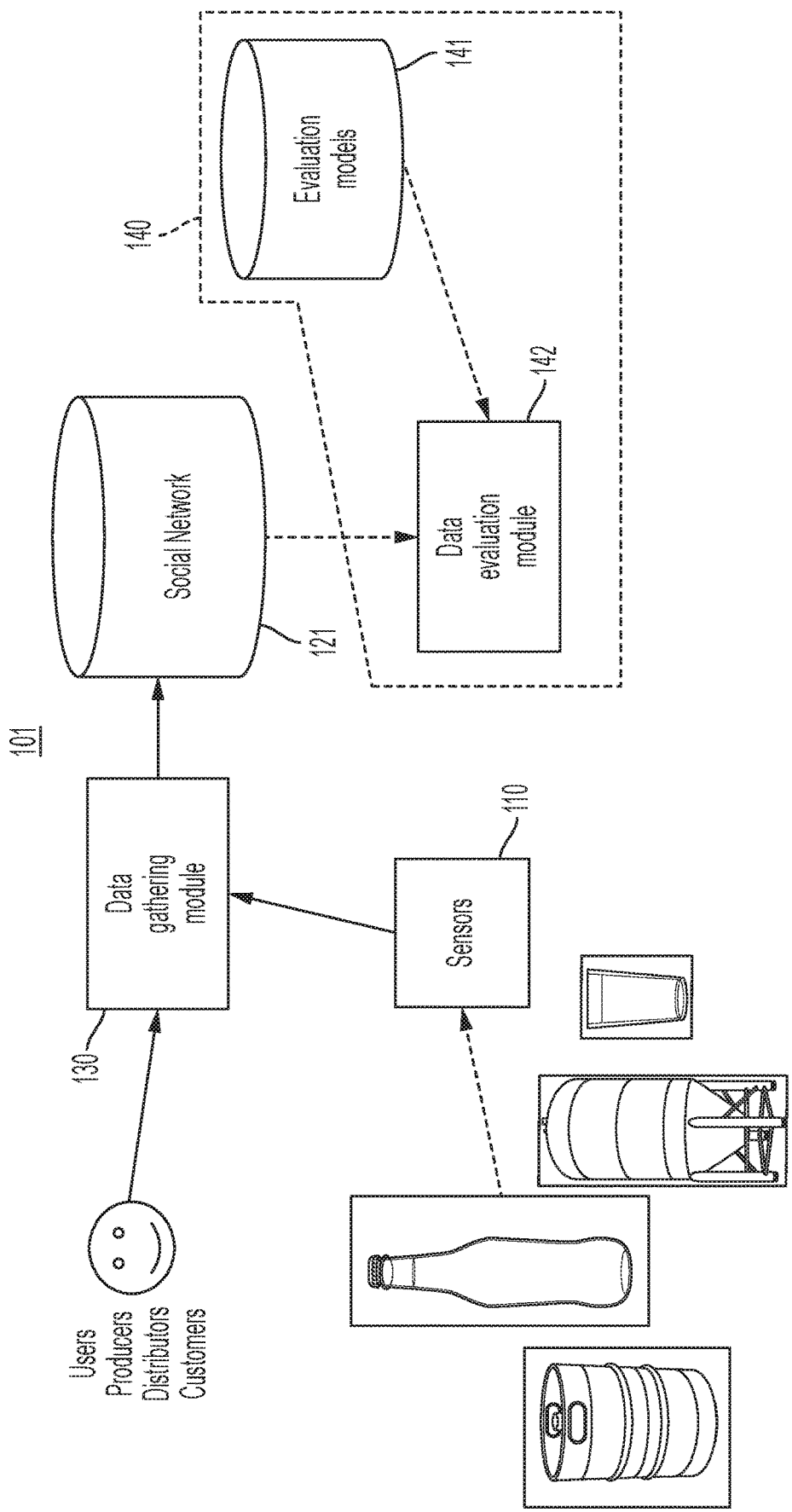
FIG. 1 depicts a system that uses sensorial traits for beverage quality analysis and control in accordance with one or more embodiments of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Although embodiments of the invention are described herein with reference to examples in which the product is a liquid beverage, embodiments of the invention are not limited to instances where the product is a liquid beverage. Persons skilled in the relevant arts will understand that the computer system and computer-implemented described herein can be applied to a variety of products, including but not limited to coffee, milk, wine or other liquors.

Turning now to an overview of technologies that are more specifically relevant to aspects of the invention, a beverage like beer has certain identifiable characteristics. These include its alcohol-by-volume (% ABV), its international bitterness units (IBUs), its standard reference method (SRM) color and its foam stability and lacing. The % ABU of a beer is the percentage of alcohol in the beer and is a function of the quantity of sugars in the wort fermented by the yeast during the fermentation process used to produce the beer. The % ABU can be determined by a hydrometer, distillation and chromatography. The IBUs of a beer measure an amount of isohumulone found in a beer in parts per million. Isohumulone is the acid found in hops that gives beer its distinct bitterness. IBUs can be measured by spectrophotometry, liquid chromatography (LC) or mass spectroscopy. The SRM color of a beer can be determined on a scale that classifies beers by color from pale straw to black and can be used as a gauge of flavor as beer color tends to relate to maltiness of beer. The SRM color of a beer can be determined by spectrophotometry or a photometer. The foam stability or lacing of a beer is a function of carbonation level, protein content, metal content and iso-alpha acid concentration and can be determined by a foam stability tester.

Other beverages besides beer, wine and liquors for instance, have similar sets of identifiable characteristics. The following description will relate generally to beer, however, for purposes of clarity and brevity.

Once beer is produced and enters the supply chain, beer quality can suffer over time until it is consumed by a consumer. This is commonly due to various factors including, but not limited to, inadequate transportation and storage that are often difficult for the producer to control. Such inadequate transportation and storage can lead to light strikes on the beer, the production of dimethyl sulfide in the beer resulting from exposure to heat, oxidation, color change and undesirable foam formation resulting from shaking.

Additional problems with beer production and marketing are that, while beers can be classified into different families and styles, it is often only experts that are able to reliably identify those families and styles. This can lead to situations where non-experts are given opportunities to provide misleading reviews.

Turning now to an overview of the aspects of the invention, one or more embodiments of the invention address the above-described shortcomings of the prior art by providing computer systems and computer-implemented methods in which sensorial traits of a beverage, such as beer, are used for quality analysis and control. The system includes various sensors and measurement devices that determine objective characteristics of beer at various stages of the supply chain. The objective characteristics are sent to a central repository by way of a network (i.e., a social network). Processor systems at the central repository perform various computer-based quality analysis and control based on the objective characteristics.

The above-described aspects of the invention address the shortcomings of the prior art by providing for computer systems and computer-implemented methods for tracking objective characteristics of beer throughout the supply chain to determine whether there are points along the supply chain where beer quality tends to degrade and to further determine how to avoid those points or how to mitigate the degradation.

Figure 2:
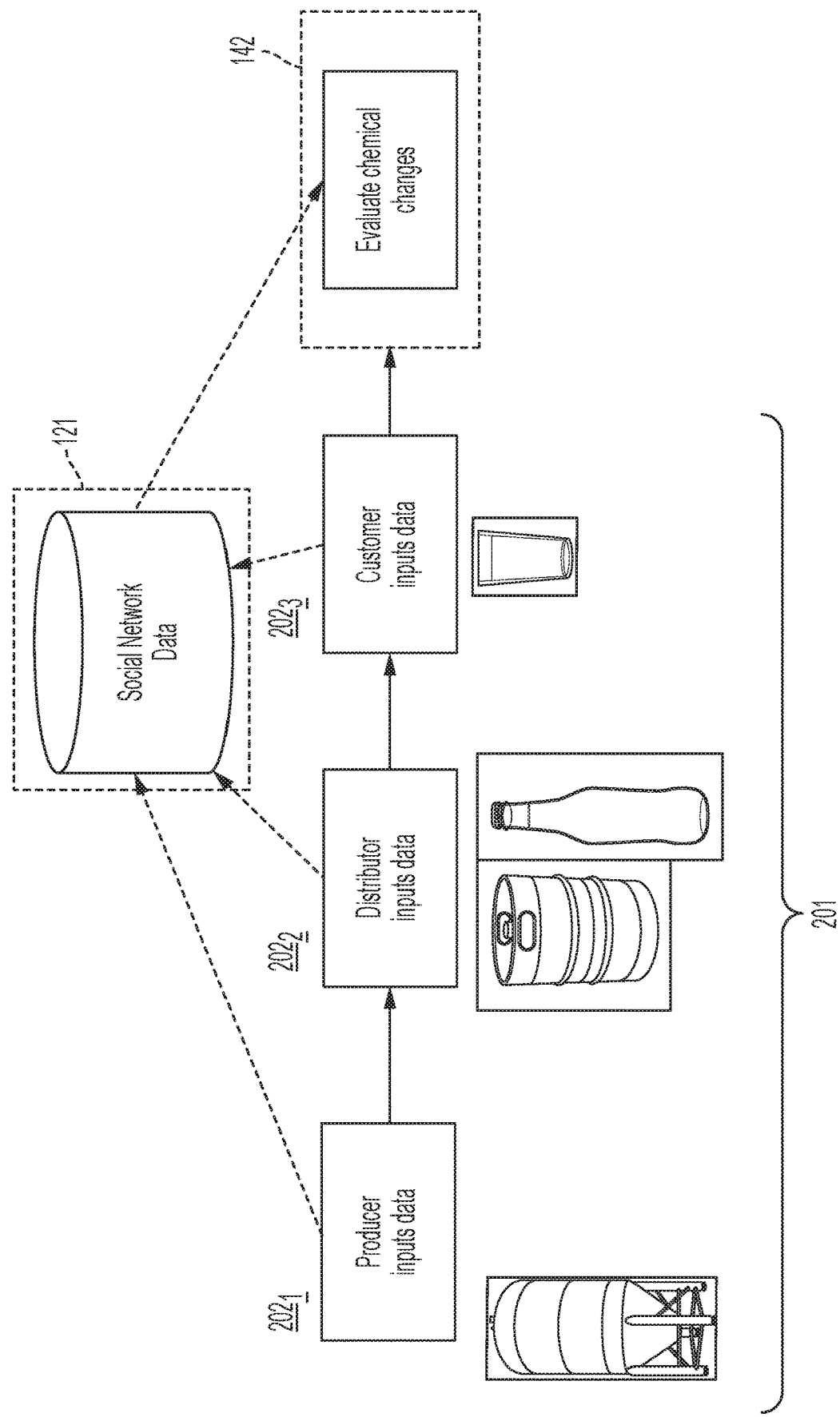
FIG. 2 depicts a flow of data throughout the system of FIG. 1 in accordance with one or more embodiments of the present invention.

Turning now to a more detailed description of aspects of the present invention, FIG. 1 is a schematic illustration of a beverage quality analysis and control system 101 in accordance with one or more embodiments of the present invention, and FIG. 2 is a schematic illustration of a flow of data throughout the beverage quality analysis and control system 101 of FIG. 1 in accordance with one or more embodiments of the present invention. The beverage quality analysis and control system 101 of FIG. 1 is provided for use with a supply chain data gathering system 201 (see FIG. 2) configured and arranged to gathered data from producers, distributors (including retailers), and ultimate consumers of a beverage. As noted above, the present description relates to beer (i.e., a specific type of beer, such as lager, pilsner, ale, etc.) but it is to be understood that this is not required and that the beverage quality analysis and control system 101 can be provided for use with a supply chain of any product, regardless of whether or not the product is a beverage. As shown in FIG. 2, the producer data, distributor data, and consumer data are gathered at various nodes of the supply chain data gathering system 201 with the producers disposed at node $202_1$, the distributors disposed at node $202_2$ and the consumers disposed at node $202_3$. In the example of FIG. 2, the producers produce beer at node $202_1$, and the distributors at node $202_2$ distribute the beer from node $202_1$ to the consumers at node $202_3$. It is to be understood, however, that this is not required and that other supply chain configurations are possible. For example, consumers can be disposed at the production facilities at node $202_1$ and the distributors can linearly or non-linearly distribute the beer to multiple nodes $202_2$ along the supply chain data gathering system 201.

With continued reference to FIG. 1, the beverage quality analysis and control system 101 includes sensors 110 provided at each of the nodes $202_{1-3}$ (see FIG. 2) for sensing objective qualities of a beer; a network such as a social network 121 that can be interacted with by multiple users at each of the nodes $202_{1-3}$; and a data gathering module 130 provided at each of the nodes $202_{1-3}$ for gathering data of the objective qualities from the sensors 110 and for forwarding the data to the social network 121 and a processing system 140. Each data gathering module 130 can include a portable computing device or smartphone 400 (see FIG. 4) with image processing capability and a display that is capable of displaying an interactive graphical user interface (GUI) of an application of the beverage quality analysis and control system 101. The processing system 140 is coupled to the network 120 and thereby receptive of the data gathered by each data gathering module 130 via the network 120. The processing system 140 includes a processing circuit and a memory on which executable instructions are stored and in which a model repository 141 is provided. The executable instructions are readable and executable by the processing circuit such that, when the executable instructions are read and executed by the processing circuit, the executable instructions cause the processing circuit to operate as a data evaluation module 142 and to execute a method of using sensorial traits for beverage quality analysis and control as described herein. In particular, when the executable instructions are read and executed by the processing circuit, the executable instructions cause the processing circuit to operate as a data evaluation module 142 and to select, from the model repository 141, a model associated with a type of the beer and to use the selected model to analyze the data gathered by each data gathering module 130 to identify changes in the objective qualities of the beer along the supply chain data gathering system 201 (see FIG. 2).

In some cases, the data evaluation module 142 can be configured to use the selected model to analyze the data gathered by each data gathering module 130, geo-location data and time data to more clearly and specifically identify the changes in the objective qualities along the supply chain data gathering system 201 and to identify where and when those changes in the supply chain data gathering system 201 occur. In some additional cases, the data evaluation module 142 can be further configured to correlate the data gathered from each data gathering module 130 with subjective quality data obtained from various expert and non-expert users.

Figure 3:
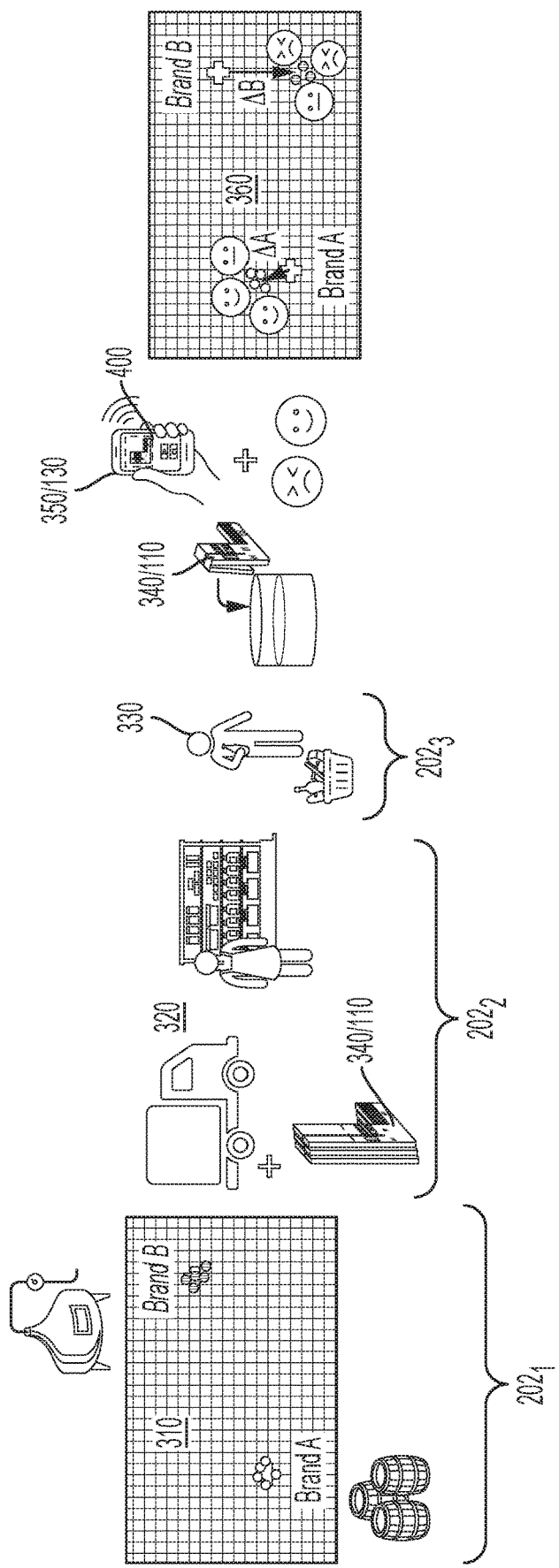
FIG. 3 depicts a particular use case of the system of FIG. 1 in which brands of beer are produced, distributed and consumed at various stages of a supply chain in accordance with one or more embodiments of the present invention.

With reference to FIG. 3, a particular use case of the system of FIG. 1 is provided in which brands of beer are produced or brewed at a brewery 310, distributed via various modes of transportation by distributors 320 and consumed by consumers 330 at the various nodes of the supply chain 301 in accordance with one or more embodiments of the present invention. As shown in FIG. 3, sensors 340 (i.e., the sensors 110 of FIG. 1) and data gathering modules 350 (i.e., the data gathering modules 130 of FIG. 1) are available to the producers in the brewery 310, the distributors 320 and the consumers 330. The sensors 340 can be used to sense objective qualities of the beer at the various nodes of the supply chain 301. The data gathering modules 340 can be used to gather data of the objective qualities generated by the sensors 330, to gather subjective data of the beer through inputs by users, to gather geo-location data and to gather time data. The data gathering modules 340 can further be used to forward the gathered data to the network (i.e. the social network 121 of FIG. 1 but not shown specifically in FIG. 3). The data can then be analyzed with results 360 of the analysis made available to the producers, the distributors 320 and the consumers 330.

Figure 4:
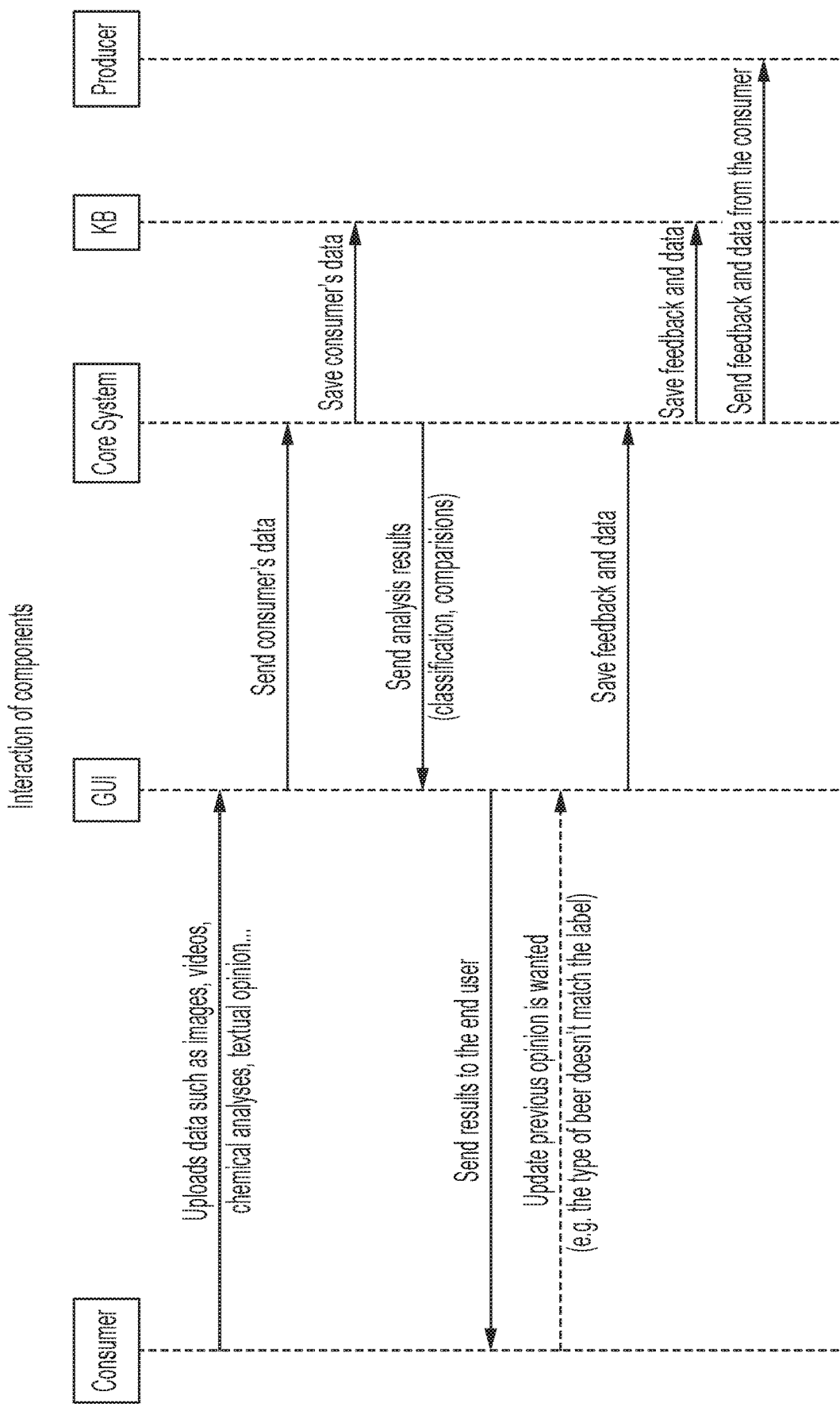
FIG. 4 is a schematic illustration of component interactions in the system of FIG. 1 in accordance with one or more embodiments of the present invention.

The flow of data in the particular use case of FIG. 3 is illustrated in FIG. 4, which is a schematic illustration of component interactions in accordance with one or more embodiments of the present invention. As shown in FIG. 4, a consumers uses his smartphone to take an image of a sensor and then uploads data, such as images, videos, certain chemical analysis data, textual opinions, etc., by way of a GUI associated with a network (i.e., the network 120 of FIG. 1). The GUI sends the user data to a core system (i.e., the processing system 140 of FIG. 1), which saves the user data in a data repository, and which analyzes the data along with other data and other user data. The core system then sends analysis results back to the consumers via the GUI whereupon the consumers can update his data and send that updated data back to the core system via the GUI. The core system then saves the updated data in the data repository and sends feedback and collected data to the producer and/or the distributor. The producer can then adjust his production/brewing methods to improve his product. The distributor receiving the feedback can adjust their distribution capabilities and storage or refrigeration systems.

Figure 6:
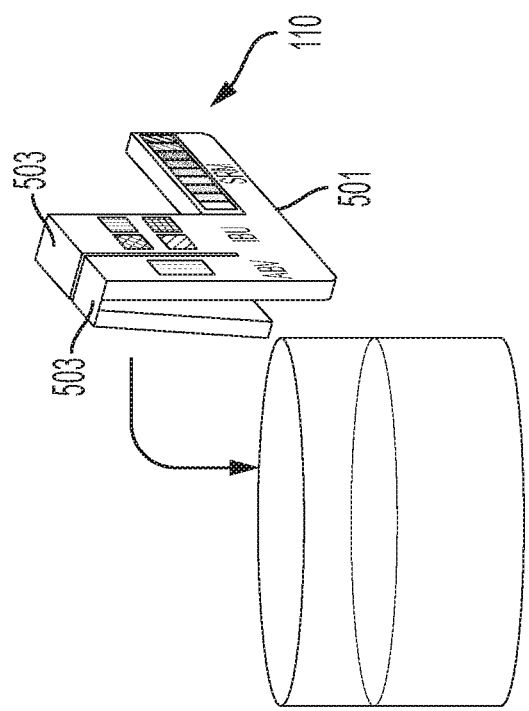
FIG. 6 is a perspective view of the sensor element of FIG. 5 being attached to a beverage in accordance with one or more embodiments of the present invention.
Figure 7:
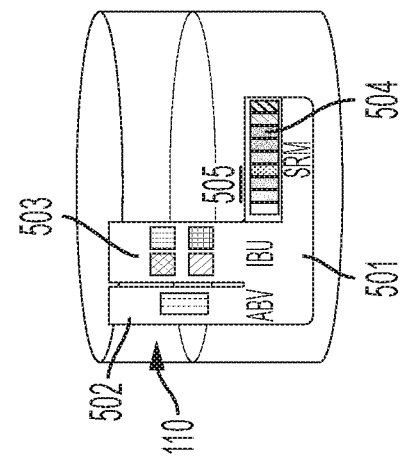
FIG. 7 is a perspective view of the sensor element of FIG. 5 having been attached to a beverage and now in use in accordance with one or more embodiments of the present invention.
Figure 5:
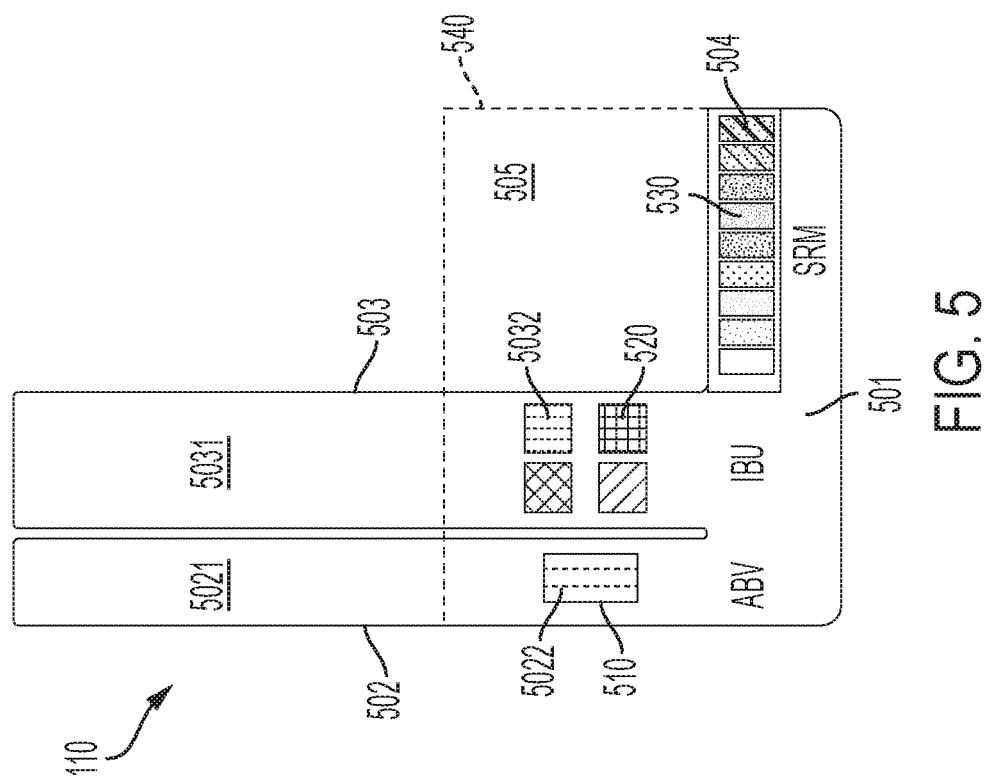
FIG. 5 is a front view of a sensor element for use in the use case of FIG. 3 in accordance with one or more embodiments of the present invention.

With reference to FIGS. 5-7, each sensor 110 of FIG. 1 can include a number of sensor elements that is sufficient to cooperatively classify the beverage. That is, in the case of the beverage being beer, each sensor 110 can include one or more of an alcohol level sensor 510, a bitterness sensor 520, a visual color chart 530 and a foam stability capture feature 540. In greater detail, as shown in FIG. 5, each sensor 110 can be made of a paper product and can include a stem 501, a first foldable strip 502 that extends from a first section of the stem 501, a second foldable strip 503 that is separate from the first foldable strip 502 and extends from a second section of the stem 501, a first visual sensor 504 disposed on the stem 501 and a second visual sensor 505 partially framed by the stem 501. The first foldable strip 502 can include an alcohol level sensor 5021 and an alcohol level indicator 5022 coupled with the alcohol level sensor 5021. The second foldable strip 503 can include a bitterness sensor 5031 and a bitterness indicator 5032 coupled with the bitterness sensor 5031. Each of the first and second foldable strips 502 and 503 is configured to be folded and anchored at the fold on a beer container rim as shown in FIG. 6 with the alcohol level sensor 5021 and the bitterness sensor 5031 deposited in the beer and the alcohol level indicator 5022 and the bitterness indicator 5032 disposed at an exterior of the beer container. The visual color chart 530 is disposed on the stem 501 and the foam stability capture feature 540 is partially framed by the stem 501. With the construction described herein, any user at a production facility of the beer, a user involved in distribution of the beer and a user or consumers consuming the beer can place the sensor 110 on a glass and take a picture of the sensor 110 and the beer with his smartphone. The image will then include a readout of the alcohol level indicator 5022, a readout of the bitterness indicator 5032, a comparable view of the beer against the visual color chart 530 and a view or video of the stability of the foam of the beer in the foam stability capture feature 540. The image can be forward to the network 120 of FIG. 1 along with at least one of geo-location data that identifies where the image was taken (i.e., along the supply data gathering system chain 201 of FIG. 2), time data that identifies when the image was taken and subjective data of the quality of the beer that is provided by the user.

Once a predetermined amount of data is received by the processing system 140 of FIG. 1, the data evaluation module 142 can select a model from the model repository 141 which is associated with for example the type of the beer (i.e., pilsner, lager, ale, etc.) and then determine how, where and when the objective qualities of the beer have changed along the supply chain data gathering system 201 of FIG. 2 in a manner that would be unexpected given the selected model. That is, if the selected model would normally predict a color change over a certain period of time for the beer, the visual color data gathered from all of the users should reveal the predicted color change. Thus, if the data suggests that a larger than expected color change occurs at some point along the supply chain data gathering system 201, the users at the production facility or the users involved in distribution can be alerted and subsequently take actions to mitigate future unpredicted color changes. On the other hand, if the subjective data from the consumer suggests that the unexpected color change is paradoxically positive, the users at the production facility or the users involved in distribution might decide not to mitigate. Alternatively, if no substantial changes from the stored models is observed in the objective qualities of the beverage from data gathered by the sensors, but the subjective data gathered from the consumers is nonetheless negative, that can also inform the production decision of the producer.

Figure 8:
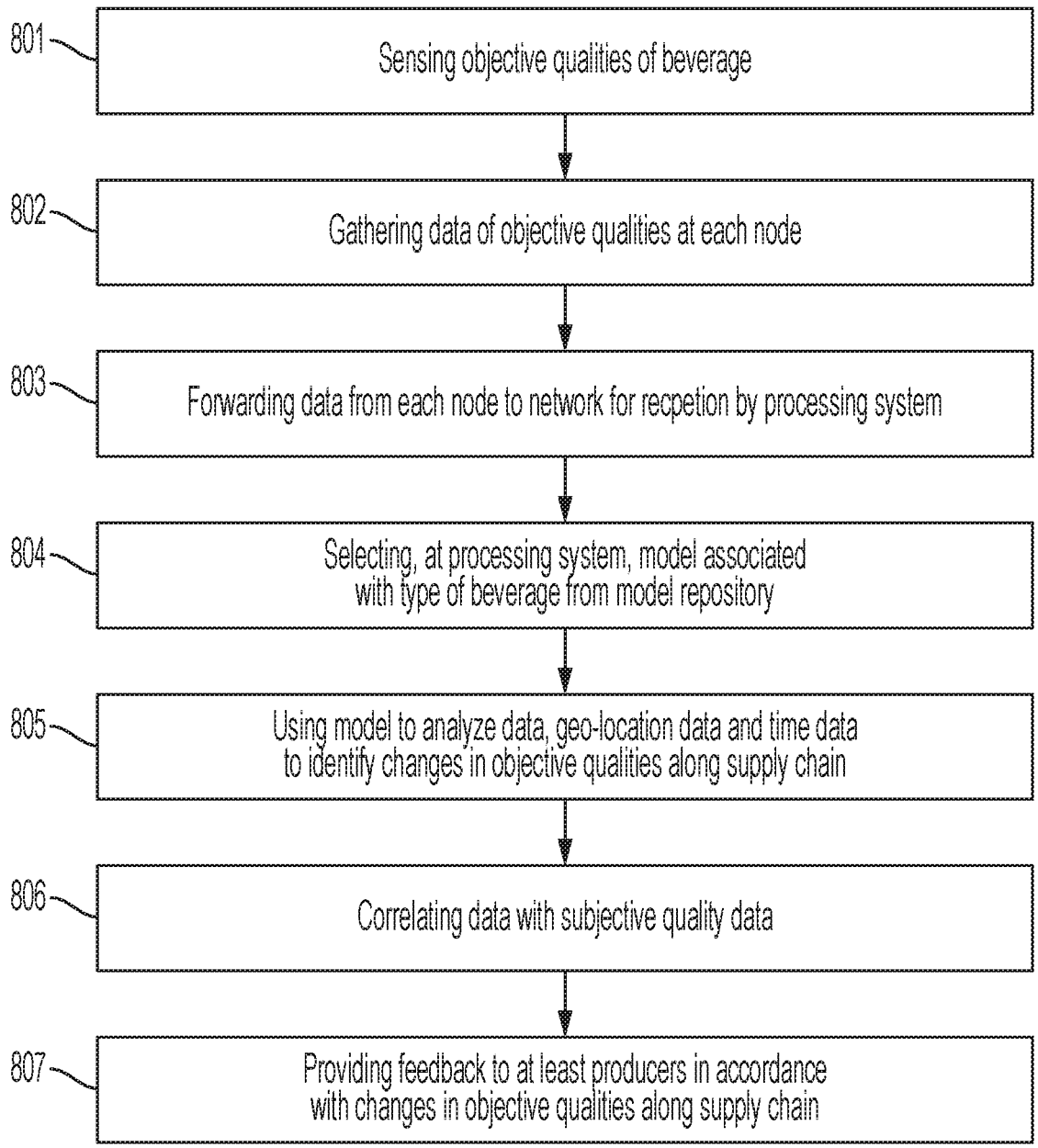
FIG. 8 is a flow diagram illustrating a method of using sensorial traits for beverage quality analysis and control in accordance with one or more embodiments of the present invention.

With reference to FIG. 8, a beverage quality analysis and control method for use with a supply chain of producers, distributors and consumers at nodes of the supply chain is provided. As shown in FIG. 8, the method includes sensing objective qualities of a beverage at each node 801 by at least one of sensing a number of the objective quantities sufficient to classify the beverage and sensing one or more of an alcohol level, a bitterness, a visual color and a foam stability of the beverage. The method further includes gathering data of the objective qualities at each node by imaging readouts of sensors at each node 802 and forwarding the data from each node to a network for reception by a processing system 803. The method also includes selecting, at the processing system, a model associated with a type of the beverage from a model repository 804 and using the model to analyze the data, geo-location data and time data to identify changes in the objective qualities along the supply chain 805. The method can further include correlating the data with subjective quality data 806 and providing feedback to at least the producers in accordance with the changes in the objective qualities along the supply chain 807.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A product quality analysis and control system, comprising:
    a processing system configured to receive data of objective qualities of a product from multiple data gathering modules,
    each of the multiple data gathering modules being respectively positioned at corresponding nodes of a supply chain and configured to receive from sensors data of objective qualities of a product when the product is at each of the corresponding nodes, and
    wherein:
    the processing system is configured to analyze the data to identify changes in the objective qualities along the supply chain, and
    each sensor comprises:
    a stem;
    one or more foldable strips extending from the stem and comprising a sensor element to sense an objective quality of the product and an indicator element to be indicative of a reading of the sensor element,
    wherein each of the one or more foldable strips is configured to be anchored on a container rim with the sensor and indicator elements in and outside the product, respectively; and
    one or more visual sensors disposed on or partially framed by the stem.

2. The product quality analysis and control system according to claim 1, further comprising a social network by which the processing system and the data gathering modules are communicative.

3. The product quality analysis and control system according to claim 1, wherein each data gathering module comprises a portable computing device with image processing capability.

4. The product quality analysis and control system according to claim 1, wherein each data gathering module comprises a smartphone with image processing capability.

5. The product quality analysis and control system according to claim 1, wherein the processing system is configured to analyze the data, geo-location data and time data to identify the changes in the objective qualities along the supply chain.

6. The product quality analysis and control system according to claim 5, wherein the processing system is further configured to correlate the data with subjective quality data.

7. The product quality analysis and control system according to claim 1, wherein each sensor comprises a number of sensors sufficient to cooperatively classify the product.

8. The product quality analysis and control system according to claim 1, wherein each sensor comprises one or more of an alcohol level sensor, a bitterness sensor, a visual color chart and a foam stability capture feature.

9. The product quality analysis and control system according to claim 1, wherein:
    the one or more foldable strips comprise:
        a first foldable strip comprising an alcohol level sensor and an alcohol level indicator coupled with the alcohol level sensor; and a second foldable strip separate from the first foldable strip and comprising a bitterness sensor and a bitterness indicator coupled with the bitterness sensor, and the one or more visual sensors comprise a visual color chart disposed on the stem and a foam stability capture feature partially framed by the stem.

10. A sensor for use in a beverage quality analysis and control system and comprising:

a stem;

one or more foldable strips respectively extending from the stem and respectively comprising a sensor element to sense an objective quality of the beverage and an indicator element to be indicative of a reading of the sensor element, wherein each of the one or more foldable strips is configured to be anchored on a beverage container rim with the sensor and indicator elements in and outside the beverage, respectively; and one or more visual sensors disposed on or partially framed by the stem.

11. The sensor according to claim 10, wherein the one or more foldable strips comprise:

a first foldable strip, which extends from a first section of the stem; and a second foldable strip, which extends from a second section of the stem and is separate from the first foldable strip.

12. The sensor according to claim 11, wherein:

the first foldable strip comprises an alcohol level sensor and an alcohol level indicator coupled with the alcohol level sensor; and the second foldable strip comprises a bitterness sensor and a bitterness indicator coupled with the bitterness sensor.

13. The sensor according to claim 10, wherein the one or more visual sensors comprise:

a visual color chart disposed on the stem; and a foam stability capture feature partially framed by the stem.

14. A beverage quality analysis and control method for use with a supply chain of producers, distributors and consumers at nodes of the supply chain, the method comprising:

sensing objective qualities of a beverage at each node;

gathering data of the objective qualities at each node and forwarding the data from each node to a network for reception by a processing system; and analyzing the data to identify changes in the objective qualities along the supply chain, wherein the sensing comprises at least one of:

sensing a number of the objective quantities sufficient to classify the beverage; and sensing one or more of an alcohol level, a bitterness, a visual color and a foam stability of the beverage.

15. The method according to claim 14, wherein the gathering of the data of the objective qualities at each node comprises imaging readouts of sensors at each node.

16. The method according to claim 14, wherein the analyzing comprises analyzing the data, geo-location data and time data to identify the changes in the objective qualities along the supply chain.

17. The method according to claim 14, further comprising correlating the data with subjective quality data.

18. The method according to claim 14, further comprising providing feedback to at least the producers in accordance with the changes in the objective qualities along the supply chain.

* * * * *